United States Patent [19]
Adolf et al.

[11] 4,056,485
[45] Nov. 1, 1977

[54] STABLE COLORED REFERENCE STANDARD FOR ENZYMATIC DETERMINATIONS

[75] Inventors: Paul K. Adolf, Easton, Pa.; James J. Carroll, East Hanover, N.J.

[73] Assignee: Warner-Lambert Company, Morris Plains, N.J.

[21] Appl. No.: 655,180

[22] Filed: Feb. 4, 1976

Related U.S. Application Data

[63] Continuation-in-part of Ser. No. 512,261, Oct. 4, 1974, abandoned.

[51] Int. Cl.$^2$ .................. C09K 3/00; G01N 31/06; G01N/31/14; G01N 31/22
[52] U.S. Cl. .................. 252/408; 23/230 B; 195/103.5 R; 356/243; 424/7
[58] Field of Search .............. 252/408; 23/230 B; 195/103.5 R, 99; 424/7, 94; 356/243

[56] References Cited

U.S. PATENT DOCUMENTS

| | | | |
|---|---|---|---|
| 2,996,436 | 8/1961 | Broida et al. | 195/103.5 R |
| 3,326,777 | 6/1967 | Babson | 195/103.5 R |
| 3,732,147 | 5/1973 | Fosker et al. | 195/103.5 R |
| 3,764,478 | 10/1973 | Bergmeyer | 195/103.5 R |
| 3,791,931 | 2/1974 | Thum et al. | 195/103.5 R |
| 3,867,259 | 2/1975 | Forgione | 195/103.5 R |

OTHER PUBLICATIONS

Babson, A. L. & Phillips, G. E.; Clin. Chim. Acta., vol. 12, pp. 210–215, (1965).

*Primary Examiner*—Benjamin R. Padgett
*Assistant Examiner*—T. S. Gron
*Attorney, Agent, or Firm*—Albert H. Graddis; Frank S. Chow; Anne M. Kelly

[57] ABSTRACT

A stable, colored reference standard suitable for use in diagnostic determinations involving enzymatic reactions in which colorless 2-(p-iodophenyl)-3-(p-nitrophenyl)-5-phenyltetrazolium chloride is reduced to the red-colored 1-(p-iodophenyl)-5-(p-nitrophenyl)-3-phenylformazan, is described. The reference standard of this invention is an aqueous solution containing, in specified amounts, 1-(p-iodophenyl)-5-(p-nitrophenyl)-3-phenylformazan; serum albumin; an N,N'-dimethylformamide or a dimethylsulfoxide solvent; and isopropyl alcohol. An inert bulking agent may be added to the aqueous colored standard and the solution obtained may then be lyophilized. The lyophilized form of the colored reference standard is stable for at least 3 months at 4° C. and 24° C. and can be easily reconstituted with water or with dilute aqueous hydrochloric acid solutions. The novel colored reference standard solution has an absorbence maximum of 500 nanometers. The colored reference standard of this invention may be used in the determination of serum lactate dehydrogenase, creatine phosphokinase, glucose-6-phosphate dehydrogenase, adenosine phosphate, glucose, glucose-6-phosphate, 6-phosphogluconate and the like.

15 Claims, No Drawings

STABLE COLORED REFERENCE STANDARD FOR ENZYMATIC DETERMINATIONS

CROSS REFERENCE TO RELATED APPLICATIONS

This application is a continuation-in-part of U.S. Ser. No. 512,261, filed Oct. 4, 1974, now abandoned.

BACKGROUND OF THE INVENTION

Methods for the quantitative determination of certain enzymes are based on the production of NADH (reduced nicotinamide adenine dinucleotide) or NADPH (reduced nicotinamide adenine dinucleotide phosphate) as a result of the enzymatic reaction on a substrate; the NADH or NADPH in turn reduces colorless 2-(p-iodophenyl)-3-(p-nitrophenyl)-5-phenyltetrazolium chloride (commonly known as INT) in the presence of an electron carrier such as phenazine methosulfate, to 1-(p-iodophenyl)-5-(p-nitrophenyl)-3-phenylformazan (commonly known as INT formazan), which is bright red and can be measured spectrophotometrically. Concentrations of enzyme are determined by simultaneously running the test reaction on a reference sample containing known quantities of the enzyme and comparing spectrophotometric readings of the unknown against the reference sample.

Representative enzymatic determinations in which the above-described general method is used include the following: Babson, A. L. and Phillips, G. E., "*A Rapid Colorimetric Assay for Serum Lactic Dehydrogenase*," Clin. Chim. Acta 12, 210–215 (1965); Van Der Veen et al., "*Isoenzymes of Creatine Phosphokinase in Tissue Extracts and in Normal and Pathological Sera,*" Clin. Chim. Acta 13, 312–316(1966); and Nachlas, M. M. et al., "*The Determination of Lactic Dehydrogenase with a Tetrasodium Salt,*" Anal. Biochem., 1, 317–326 (1960).

The colored reference standard of this invention is useful not only in the determination of enzymatic activity but also for the determination of substrates or other products involving coupled enzymatic reactions yielding formazan. Thus, the colored reference standard of this invention may be used in any determination in which colorless 2-(para-iodophenyl)-3-(para-nitrophenyl)-5-phenyltetrazolium chloride is reduced to the bright red 1-(p-iodophenyl)-5-(p-nitrophenyl)-3-phenylformazan by means of enzymatic coupling reactions. For example, in the determination of glucose wherein INT formazan is produced via the hexokinase/glucose 6-phosphate dehydrogenase reaction; and in the diagnostic determination of such materials as adenosine triphosphate, glucose-6-phosphate, 6-phosphogluconate and the like, which involve similar reactions yielding INT formazan, the colored reference standard of this invention may be used to standardize the quantities of test product found in an unknown sample.

The accuracy of results using aforementioned methods for determining enzymatic activities depends, to a large extent, on the preparation and stability of the reference sample containing the known quantity of enzyme against which results with the test sample are compared. Furthermore, these enzymatic test methods involve double work, since in every instance, the test itself must be run on the reference sample, as well as on the unknown sample. such duplication requires extensive checking in order to insure that inaccuracies have not occurred.

Thus, the need for and the advantages of a stable colored reference standard for use in enzymatic determinations without simultaneous running of a control are obvious. However, such a product is not commercially available.

SUMMARY OF THE INVENTION

A stable colored reference standard comprises an aqueous solution containing from 0.001% to 0.020% by weight, based on the weight of the total solution of 1-(p-iodophenyl)-5-(p-nitrophenyl)-3-phenylformazan, from 0.01% to 0.10% by weight of serum albumin, from 1.76% to 10% by weight of a solvent such as N,N'-dimethylformamide or dimethylsulfoxide and from 1.45% to 10% by weight of isopropyl alcohol. From 5% to 20% by weight of an inert bulking agent may be added to the aqueous colored reference standard solution, which may then be lyophilized. The lyophilized product contains from 0.0116% to 0.231% by weight of the total dried product, of 1-(p-iodophenyl)-5-(p-nitrophenyl)-3-phenyl-formazan, from 0.117% to 1.155% by weight of serum albumin and from 98.795% to 99.743% by weight of dextran, and may be easily reconstituted with water. The aqueous colored referece standard solution has an absorbence maximum at 500 nanometers and is suitable for use in the determination of serum lactate dehydrogenase, creatine phosphokinase, glucose-6-phosphate dehydrogenase, adenosine phosphate, glucose, glucose-6-phosphate, 6-phosphogluconate and the like.

DESCRIPTION OF THE INVENTION

It has now been found that a colored reference standard suitable for use in diagnostic determinations involving certain enzyme reactions may be prepared to contain, in an aqueous solution, from 0.001% to 0.020% by weight, based on the weight of the total solution of 1-(p-iodophenyl)-5-(p-nitrophenyl)-3-phenylformazan, from 0.01% to 0.10% by weight of serum albumin, from 1.76% to 10% by weight of a solvent selected from the group consisting of N,N'-dimethylformamide and dimethylsulfoxide, and from 1.45% to 10% by weight of isopropyl alcohol, which has an absorbence maximum of 500 nanometers. The addition of from 5% to 20% by weight of an inert bulking agent provides a solution which can be lyophilized. The dried lyophilized form of the colored reference standard contains from 0.0116% to 0.231% by weight, based on the total weight of the dried product, of 1-(p-iodophenyl)-5-(p-nitrophenyl)-3-phenylformazan, from 0.117% to 1.155% by weight of serum albumin and from 98.795% to 99.743% by weight of inert bulking agent. Quantities of one ingredient in the dried lyophilized form of the product of this invention will vary, within the above-stated ranges for that ingredient, depending on the amounts of other ingredients present since all ranges are expressed as percent by weight, based on the total weight of the dried product. The lyophilized product is stable for at least 3 months at 4° C. and 24° C., and may be reconstituted with water to form a clear solution which can be utilized, without difficulty, as a reference standard in enzymatic determinations.

The 1-(p-iodophenyl)-5-(p-nitrophenyl)-3-phenylformazan in the colored reference standard of this invention (commonly known as INT formazan) is commercially available (National Biochemicals Corp., Cleveland, Ohio) and has the following formula:

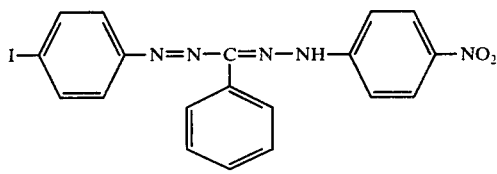

INT formazan is frequently encountered in microbiological identification techniques, particularly for the examination of foods and pathological specimens where bacteria, if present reduce the colorless 2-(p-iodophenyl)-3-(p-nitrophenyl)-5-phenyltetrazolium chloride (commonly known as INT) which has the formula:

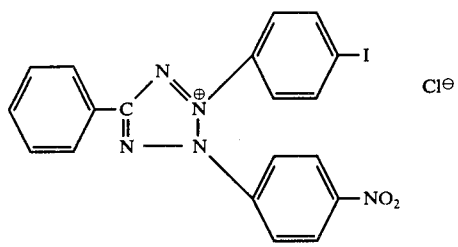

to the brightly colored INT formazan. Additionally, certain enzymatic reactions will cause the reduction of INT to INT formazan and it is in the determination of these enzymes that the colored reference standard of the invention finds utility.

The solvents which have been found to improve the solubility characteristics of INT formazan and to permit easy reconstitution with water after lyophilization include N,N'-dimethylformamide or dimethylsulfoxide. The addition of isopropyl alcohol also aids in this solubilizing process. It is of considerable importance that these solvents do not interfere with the absorbence maximum of the aqueous colored reference standard.

The stable, colored reference standard of this invention also contains serum albumin. Bovine serum albumin is preferred. This material is believed to aid in stabilizing both the lyophilized and aqueous forms of the reference standard.

Suitable inert bulking agents for use in the reference standard of this invention include natural and synthetic gums such as gum arabic, sodium alginate, extract of Irish moss, carboxymethyl cellulose, polyvinyl pyrrolidinone and the like; sugars such as sorbitol, mannitol, sucrose and the like; and carbohydrates such as starch, dextran and the like. The preferred bulking agent is a dextran having a molecular weight of approximately 10,000.

A preferred colored reference standard may be prepared according to the practice of this invention by forming an aqueous solution containing 0.005% to 0.015% by weight, based on the weight of the total solution of 1-(p-iodophenyl)-5-(p-nitrophenyl)-3-phenylformazan; from 0.02% to 0.075% by weight of bovine serum albumin; 1.76% to 10% by weight of N,N'-dimethylformamide; and from 1.45% to 10% by weight of isopropyl alcohol. If the lyophilized form of the colored reference standard is to be prepared, from 8% to 14% by weight of dextran having a molecular weight of approximately 10,000 is added to the aqueous solution. The dried lyohilized form of the preferred colored reference standard contains from 0.0580% to 0.174% by weight, based on the total weight of the dried product, of 1-(p-iodophenyl)-5-(p-nitrophenyl)-3-phenylformazan, from .233% to .869% of bovine serum albumin and from 99.266% to 99.607% of dextran having a molecular weight of approximately 10,000.

A particularly preferred colored reference standard, according to the teachings of this invention, contains, in an aqueous solution, 0.0094% by weight, based on the weight of the total solution, of 1-(p-iodophenyl)-5-(p-nitrophenyl)-3-phenylformazan; 0.056% by weight of bovine serum albumin; 3.02% by weight of N,N'-dimethylformamide and 7.48% by weight of isopropyl alcohol. For lyophilization, dextran is added to the above aqueous solution and the preferred solution of the colored reference standard contains, before lyophilization, 0.0086% by weight, based on the weight of the total solution, of 1-(p-iodophenyl)-5-(p-nitrophenyl)-3-phenylformazan; 0.051% by weight of bovine serum albumin; 8.21% by weight dextran having a molecular weight of approximately 10,000; 2.77% by weight of N,N'-dimethylformamide and 6.86% by weight of isopropyl alcohol in an aqueous solution.

After lyophilization, the dried product contains, in the most preferred embodiment of this invention, 0.104% by weight of 1-(p-iodophenyl)-5-(p-nitrophenyl)-3-phenylformazan; 0.622% by weight of bovine serum albumin; and 99.27% by weight of dextran having a molecular weight of approximately 10,000.

The lyophilized form of the colored reference standard of this invention has been found to be stable for at least 3 months at temperatures of 4° C. and 24° C. The lyophilized standard, reconstituted with water or 0.1 N hydrochloric acid, is easily handled for dilutions which may be required to construct standard curves for fixed-point colorimetric enzymatic assays. Reconstituted colored reference standard solutions are stable for eight hours at room temperature, and for at least 48 hours at 4° C.

The absorbence of the reconstituted form of aforementioned most preferred color reference standard, at 500 nanometers, is approximately 0.80. Various absorbence values can be obtained by varying the amount of 1-(p-iodophenyl)-5-(p-nitrophenyl)-3-phenylformazan to reflect levels of enzymatic activity in a particular test or in coupled enzymatic reactions in which the colored reference standard of this invention is to be used.

In order to prepare the stable color reference standard of this invention, the various ingredients named above must be added one to the other in a particular fashion to obtain a product having the necessary stability and solubility to permit reconstitution after lyophilization. Such characteristics are achieved by first dissolving the INT formazan in a selected solvent completely, then adding isopropyl alcohol, with thorough mixing; dissolving the serum albumin in water; and slowly adding the INT formazan solution to the serum albumin solution, with stirring. In the preferred embodiment of this invention, where lyophilization is desired, the inert bulking agent is dissolved in water along with the serum albumin. The final solution obtained is dispensed in aliquots and subjected to the usual lyophilization procedures.

For use in enzymatic determinations, the above described lyophilized form of the color reference standard is reconstituted with water or 0.1N hydrochloric acid. The colored reference standard solution serves as a standard of known activity against which the unknown test samples are read in order to determine the activity of enzyme in the unknown. The colored reference standard solution of the invention may be diluted, if desired, for construction of curves for the fixed point colorimetric enzymatic assays.

Thus, there is provided a colored reference standard which has excellent stability in the lyophilized state and which, upon reconstitution, is easily handled in currently used enzymatic determinations.

To further illustrate the present invention, the following examples are given:

EXAMPLE I

Preparation of the Stable Colored Reference Standard Solution

A. 9.17 mg of INT formazan is dissolved in 3.12 ml of N,N'dimethylformamide. To this solution 9.38 ml of reagent grade isopropanol is added and mixed thoroughly.

B. 8.75 g of dextran having a molecular weight of approximately 10,000 and 54.8 mg of bovine serum albumin are dissolved in 87.5 ml of purified water.

C. Solution A is added slowly to Solution B with stirring. The combined solution obtained is dispensed in 4.0 ml aliquots into 10 ml vials, frozen and lyophilized for 36 hours with a 30° C. set-point. The vials are capped under dry nitrogen. Each vial is reconstituted with 10 ml of 0.1 N hydrochloric acid and the absorbence at 500 nanometers is 0.80 ± 0.010 which represents 322 ± 4.2 International Units of lactate dehydrogenase activity at 37° C.; or 266 ± 3.3 International Units of creatine phosphokinase activity of 30° C.

EXAMPLE II

Colorimetric Assay for Serum Lactate Dehydrogenase

Reagents for the assay are prepared as follows:

Color Reagent: 50 mg of INT is dissolved in about 15 ml of water with prolonged agitation until complete dissolution is obtained. 125 mg of nicotinamide adenine dinucleotide is added and dissolved, followed by the addition of 12.5 mg phenazine methosulfate. The solution is transferred with washings immediately to a low actinic 25-ml volumetric flask and diluted with water to the mark.

Buffer Reagent: 1.0 g of ethoxylated oleyl alcohol (Lipal 10-OA, Drew Chemical Co., Boonton, N.J.) is dissolved in 10 ml of water by heating to about 95° C. The solution is diluted with water to 50 ml and 12.1 g of Tris is added. The pH is adjusted to 8.2 with 3 N HCL and then diluted to 100 ml.

Substrate Reagent: (0.1 M L(+)lactate) 5.0 ml of a 20% solution of L(+) lactic acid is added to about 50 ml of water. The pH is adjusted to 5.5 with 1 N NaOH and diluted to 120 ml with water. The solution is saturated with a few drops of chloroform.

Control Reagent: 0.2 g of potassium oxalate and 0.2 g of ethylenediaminetetraacetic acid, disodium dihydrate, are dissolved in 100 ml of water. The above preparations are described in Babson et al. Clin Chim. Acta 12: 210-215 (1965).

Procedure: 0.1 ml of serum and 0.2 ml of buffer reagent are pipetted in each of two tubes. 0.5 ml of substrate is added to one tube and 0.5 ml of control reagent is added to the other tube. Both tubes are mixed and warmed to 37° C. At precisely timed intervals, 0.2 ml of color reagent is added to both tubes, and the contents are mixed and immediately returned to the water bath. Exactly five minutes after adding color reagent, 5 ml of 0.1 N HCl is added to both tubes and the contents mixed. The difference in absorbence between the control tube and the serum sample tube, determined at 500 nm within 20 minutes is 0.67. This absorbence is compared with the colored reference standard of Example I which has an absorbence of 0.800 ± 0.010 equivalent to 322 ± 4.2 International Units of lactate dehydrogenase activity. The lactate dehydrogenase activity in the serum is calculated to be 270 International Units at 37° C.

We claim:

1. A colored reference standard for use in diagnostic determinations involving enzymatic reactions in which 1-(p-iodophenyl)-5-(p-nitrophenyl)-3-phenylformazan is produced, which comprises an aqueous solution of:
   A. From about 0.001% to about 0.020% by weight, based on the weight of the total solution, of 1-(p-iodophenyl)-5-(p-nitrophenyl)-3-phenylformazan;
   B. From about 0.01% to about 0.10% by weight of serum albumin;
   C. From about 1.76% to about 10% by weight of solvent selected from the group consisting of N,N'-dimethylformamide and dimethylsulfoxide; and
   D. From about 1.45% to about 10% by weight of isopropyl alcohol;

said aqueous color standard solution having an absorbence maximum at 500 nanometers.

2. A colored reference standard for use in diagnostic determinations involving enzymatic reactions in which 1-(p-iodophenyl)-5-(p-nitrophenyl)-3-phenylformazan is produced, which comprises an aqueous solution of;
   A. From about 0.001% to about 0.020% by weight of 1-(p-iodophenyl)-5-(p-nitrophenyl)-3-phenylformazan;
   B. From about 0.01% to about 0.10% by weight of serum albumin;
   C. From about 1.76% to about 10% by weight of solvent selected from the group consisting of N,N'-dimethylformamide and dimethylsulfoxide;
   D. From about 1.45% to about 10% by weight of isopropyl alcohol; and
   E. From about 5% to about 20% by weight of an inert bulking agent;

said percentages by weight being based on the weight of the total solution;

said aqueous colored standard solution having the absorbence maximum at 500 nanometers.

3. A colored reference standard according to claim 1 comprising an aqueous solution of:
   A. From about 0.005% to about 0.015% by weight, based on the weight of the total solution, of 1-(p-iodophenyl)-5-(p-nitrophenyl)-3-phenylformazan;
   B. From about 0.02% to about 0.0755 by weight of serum albumin;
   C. From about 1.76% to about 10% by weight of N,N'dimethylformamide; and
   D. From about 1.45% to about 10% by weight of isopropyl alcohol.

4. A colored reference standard according to claim 2 comprising an aqueous solution of:
   A. From about 0.005% to about 0.015% by weight of 1-(p-iodophenyl)-5-(p-nitrophenyl-3-phenylformazan;
   B. From about 0.02% to about 0.075% by weight of serum albumin;
   C. From about 1.76% to about 10% by weight of N,N'-dimethylformamide;

D. From about 1.45% to about 10% by weight of isopropyl alcohol; and

E. From about 8% to about 14% by weight of dextran having a molecular weight of approximately 10,000;

said percentage by weight being based on the weight of the total solution.

5. A colored reference standard according to claim 3 which comprises:
   A. About 0.0094% by weight, based on the weight of the total solution, of 1-(p-iodophenyl)-5-(p-nitrophenyl)-3-phenylformazan;
   B. About 0.056% by weight of bovine serum albumin;
   C. About 3.02% by weight of N,N'-dimethylformamide; and
   D. About 7.48% by weight of isopropyl alcohol.

6. A colored reference standard according to claim 4 which comprises
   A. About 0.0086% by weight, based on the weight of the total solution, of 1-(p-Iodophenyl)-5-(p-nitrophenyl)-3-phenylformazan;
   B. About 0.051% by weight of bovine serum albumin;
   C. About 2.77% by weight of N,N'-dimethylformamide;
   D. About 6.86% by weight of isopropyl alcohol; and
   E. About 8.21% by weight of dextran having a molecular weight of approximately 10,000.

7. A lyophilized colored reference standard for use in diagnostic determinations involving enzymatic reactions in which 1-(p-iodophenyl)-5-(p-nitrophenyl)-3-phenylformazan is produced, obtained by a process which comprises:
   A. Completely dissolving from about 0.001% to about 0.020% by weight of 1-(p-iodophenyl)-5-(p-nitrophenyl)-3-phenylformazan, in about 1.76% to 10% by weight of solvent selected from the group consisting of N,N'-dimethylformamide and dimethylsulfoxide;
   B. Adding from about 1.45% to about 10% by weight of isopropyl alcohol to (A) slowly, and mixing thoroughly;
   C. Dissolving from about 0.01% to about 0.1.0% by weight of serum albumin and from about 5% to about 20% by weight of inert bulking agent in water;
   D. Adding solution (B) to solution (C) slowly, with stirring; and
   E. Lyophilizing the solution of (D);

said percentages by weight being based on the weight of the total solution, prior to lyophilization.

8. A lyophilized colored reference standard according to claim 7 wherein, in Step (A) from about 0.005% to about 0.015% by weight of 1-(p-iodophenyl)-5-(p-nitrophenyl)-3-phenylformazan is used; and in Step C, from about 0.02% to about 0.075% by weight of serum albumin and from about 8% to about 14% by weight of dextran bulking agent having a molecular weight of approximately 10,000, are used; said percentages by weight being based on the weight of the total solution, prior to lyophilization.

9. a lyophilized colored reference standard according to claim 7 wherein in Step (A), about 0.0086% by weight of 1-(p-iodophenyl)-5-(p-nitrophenyl)-3-phenylformazan is dissolved in 2.77% by weight of N,N'-dimethylformamide; in Step B, about 6.86% by weight of isopropyl alcohol is added; and in Step C, 8.21% by weight of dextran having a molecular weight of approximately 10,000 and 0.051% by weight of bovine serum albumin are dissolved in water; said percentages by weight being based on the weight of the total solution, prior to lyophilization.

10. A process for preparing a colored reference standard for use in diagnostic determinations involving enzymatic reactions in which 1-(p-iodophenyl)-5-(p-nitrophenyl)-3-phenylformazan is produced which comprises:
    A. Completely dissolving from about 0.001% to about 0.020% by weight of 1-(p-iodophenyl)-5-(p-nitrophenyl)-3-phenylformazan, in about 1.76% to 10% by weight of solvent selected from the group consisting of N,N'-dimethylformamide and dimethylsulfoxide;
    B. Adding from about 1.45% to about 10% by weight of isopropyl alcohol to (A) slowly, and mixing throughly;
    C. Dissolving from about 0.01% to about 0.10% by weight of serum albumin in water;
    D. Adding solution (B.) to solution (C.) slowly, with stirring;

said percentages by weight being based on the weight of the total solution.

11. A process for preparing a lyophilized colored reference standard for use in diagnostic determinations involving enzymatic reactions in which 1(p-iodophenyl)-5-(p-nitrophenyl)-3-phenylformazan is produced which comprises:
    A. Completely dissolving from about 0.001% to about 0.020% by weight, of 1-(p-iodophenyl)-5-(p-nitrophenyl)-3-phenylformazan in about 1.76% to 10% by weight of solvent selected from the group consisting of N,N'-dimethylformamide and dimethylsulfoxide;
    B. Adding from about 1.45% to about 10% by weight of isopropyl alcohol to (A) slowly, and mixing thoroughly;
    C. Dissolving from about 0.01% to about 0.10% by weight of serum albumin and from about 5% to about 20% by weight of an inert bulking agent in water;
    D. Adding solution (B) to solution (C) slowly with stirring; and
    E. Lyophilizing the solution of (D);

said percentages by weight being based on the weight of the total solution, prior to lyophilization.

12. A process according to claim 11 wherein, in Step (A) from about 0.005% to about 0.015% by weight of 1-(p-iodophenyl)-5-(p-nitrophenyl)-3-phenylformazn is dissolved in from about 1.76% to about 10% by weight of N,N'-dimethylformamide; and in Step C, from about 0.02% to about 0.075% by weight of serum albumin and from about 8% to about 14% by weight of a dextran bulking agent having a molecular weight of approximately 10,000, are dissolved in water; said percentages by weight being based on the weight of the total solution, prior to lyophilization.

13. A process according to claim 12, wherein in step (A), about 0.0086% by weight of 1-(p-iodophenyl)-5-(p-nitrophenyl)-3-phenylformazan is dissolved in 2.77% by weight of N,N'-dimethylformamide; in Step B, about 6.86% by weight of isopropyl alcohol is added; and in Step C, 8.21% by weight of dextran having a molecular weight of approximately 10,000 and 0.051% by weight of bovine serum albumin are dissolved in water; said percentages by weight being based on the weight of the total solution, prior to lyophilization.

14. A process according to claim 10 wherein, in Step A from about 0.005% to about 0.015% by weight of 1-(p-iodophenyl)-5-(p-nitrophenyl)-3-phenylformamzan is dissolved in from about 1.76% to about 10% by weight of N,N'-dimethylformamide and in Step C, from about 0.02% to about 0.075% by weight of serum albumin is dissolved in water; said percentages by weight being based on the weight of the total solution.

15. A process according to claim 14 wherein, in Step A about 0.0094% by weight of 1-(p-iodophenyl)-5-(p-nitrophenyl)-3-phenylformazan is dissolved in 3.02% by weight of N,N'-dimethylformamide; in Step B, about 7.48% by weight of isopropyl alcohol is added; and in Step C, about 0.056% by weight of bovine serum albumin is dissolved in water; said percentages by weight being based on the weight of the total solution.

* * * * *

UNITED STATES PATENT OFFICE
CERTIFICATE OF CORRECTION

Patent No. 4,056,485          Dated NOVEMBER 1, 1977

Inventor(s) PAUL K. ADOLF AND JAMES J. CARROLL

It is certified that error appears in the above-identified patent and that said Letters Patent are hereby corrected as shown below:

Column 6, in Claim 3, line 54, "0.0755" should read ---0.075%---.

Column 7, in Claim 7, line 41, "0.1.0%" should read ---0.10%---.

*Signed and Sealed this*

*Fourth* Day of *July 1978*

[SEAL]

Attest:

RUTH C. MASON
*Attesting Officer*

DONALD W. BANNER
*Commissioner of Patents and Trademarks*